(12) United States Patent
Honda

(10) Patent No.: US 7,682,022 B2
(45) Date of Patent: Mar. 23, 2010

(54) OPHTHALMIC APPARATUS

(75) Inventor: Naoto Honda, Okazaki (JP)

(73) Assignee: Nidek Co., Ltd., Gamagori-shi (JP)

( * ) Notice: Subject to any disclaimer, the term of this patent is extended or adjusted under 35 U.S.C. 154(b) by 178 days.

(21) Appl. No.: 12/076,821

(22) Filed: Mar. 24, 2008

(65) Prior Publication Data

US 2008/0239239 A1 Oct. 2, 2008

(30) Foreign Application Priority Data

Mar. 30, 2007 (JP) ............................. 2007-091452

(51) Int. Cl.
*A61B 3/10* (2006.01)
(52) U.S. Cl. ...................... 351/208; 351/211
(58) Field of Classification Search ................. 351/208, 351/211, 221
See application file for complete search history.

(56) References Cited

U.S. PATENT DOCUMENTS

| | | | |
|---|---|---|---|
| 4,817,620 A | 4/1989 | Katsuragi et al. | |
| 5,381,194 A * | 1/1995 | Nishio et al. | 351/208 |
| 6,022,108 A | 2/2000 | Yoshida et al. | |
| 6,655,805 B2 * | 12/2003 | Fujieda | 351/212 |
| 2004/0189936 A1 | 9/2004 | Mimura et al. | |
| 2007/0097317 A1 | 5/2007 | Hayashi et al. | |
| 2008/0165321 A1 * | 7/2008 | Mimura et al. | 351/208 |

FOREIGN PATENT DOCUMENTS

| | | |
|---|---|---|
| EP | 1 535 567 A1 | 6/2005 |
| JP | A-01-265937 | 10/1989 |
| JP | A-10-071122 | 3/1998 |
| JP | A-2004-313758 | 11/2004 |
| JP | A-2007-144128 | 6/2007 |
| JP | A-2008-099968 | 5/2008 |
| WO | WO 2007/114426 A1 | 10/2007 |

* cited by examiner

*Primary Examiner*—Jordan M. Schwartz
(74) *Attorney, Agent, or Firm*—Oliff & Berridge, PLC

(57) ABSTRACT

An ophthalmic apparatus capable of observing an examinee's eye even during switching of measurement modes comprises a first measurement unit, a second measurement unit, an up-and-down movement mechanism, a display device, mode switching means which generates a mode switching signal for switching between a first measurement mode and a second measurement mode, and a control unit which drives and controls the up-and-down movement mechanism to change a state in which a first center axis and the eye are placed at substantially a same height into a state in which a second center axis and the eye are placed at substantially a same height by moving a main body of the apparatus, and controls to display the image outputted from a first image-pickup element and the image outputted from a second image-pickup element simultaneously on the display device during a shift from the first measurement mode to the second measurement mode.

6 Claims, 4 Drawing Sheets

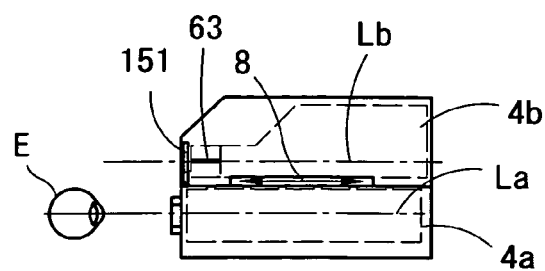
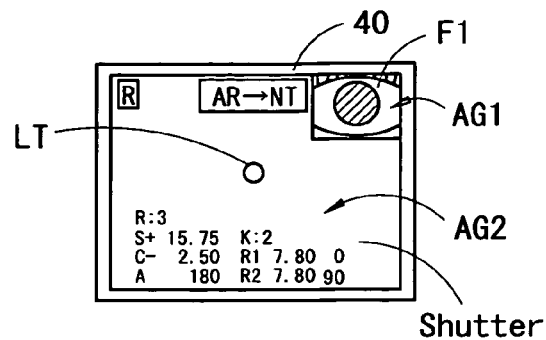
FIG. 3A  FIG. 4A
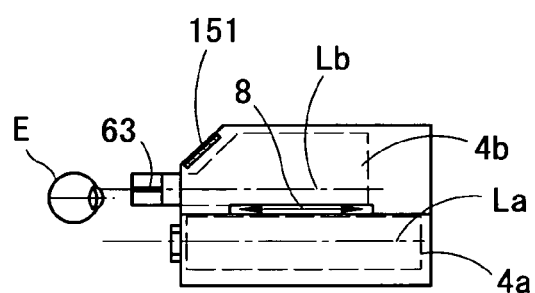
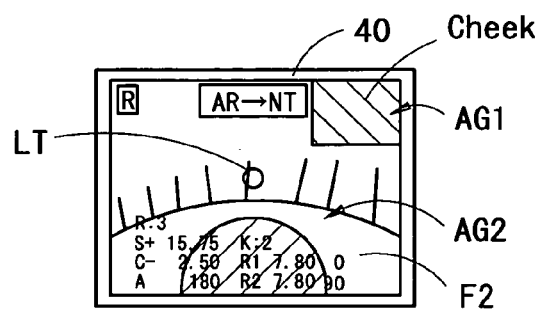
FIG. 3B  FIG. 4B
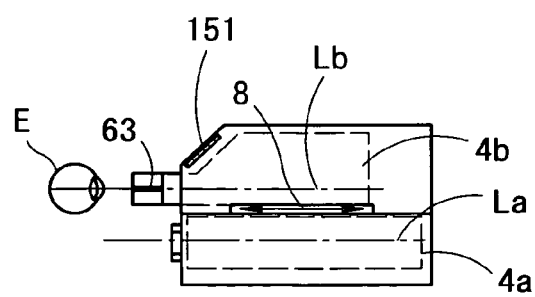
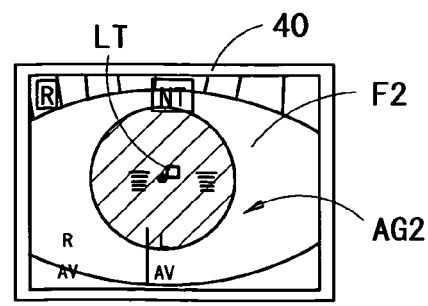
FIG. 3C  FIG. 4C

OPHTHALMIC APPARATUS

BACKGROUND OF THE INVENTION

1. Field of the Invention

The present invention relates to an ophthalmic apparatus which measures a plurality of eye characteristics of an examinee's eye.

2. Description of Related Art

Conventionally, there is known a multifunction ophthalmic apparatus comprising an intraocular pressure measurement unit which measures intraocular pressure of an examinee's eye and an eye refractive power measurement unit which measures eye refractive power of the eye, which are arranged in an up-and-down direction. This ophthalmic apparatus comprises a measurement part including separate measurement optical axes positioned in the up-and-down direction. By moving the measurement part in the up-and-down direction by an up-and-down driving unit, one of the measurement optical axes is aligned with the eye, and measurement is performed (see U.S. Pat. No. 4,817,620 corresponding to Japanese Patent Application Unexamined Publication No. Hei01-265937). In this apparatus, a television camera for picking up an image of an anterior segment of the eye is used for alignment between the eye and the apparatus. The television camera is shared by the intraocular pressure measurement unit and the eye refractive power measurement unit. The anterior-segment image picked up by the television camera is observed by an examiner using a display monitor provided on the apparatus.

In the above ophthalmic apparatus, the anterior-segment image is not displayed on the display monitor during switching of measurement modes (e.g. switching from an eye refractive power measurement mode to an intraocular pressure measurement mode). This is because the television camera is shared by the intraocular pressure measurement unit and the eye refractive power measurement unit. Consequently, the examiner cannot observe the eye during the switching of the measurement modes.

SUMMARY OF THE INVENTION

An object of the invention is to overcome the problems described above and to provide, in a multifunction ophthalmic apparatus having a plurality of measurement units, an ophthalmic apparatus capable of observing an examinee's eye even during switching of measurement modes.

To achieve the objects and in accordance with the purpose of the present invention, an ophthalmic apparatus comprises a first measurement unit placed in a main body of the apparatus, which measures a first eye characteristic of an examinee's eye, the unit comprising a first image-pickup optical system comprising a first image-pickup element which picks up an image of an anterior segment of the eye in order to observe the anterior segment of the eye, and a first alignment optical system for performing alignment between the anterior-segment image picked up by the first image-pickup element and a first center axis so as to have a predetermined relationship, a second measurement unit placed in the main body of the apparatus in a position in an up-and-down direction with respect to the first measurement unit, which measures a second eye characteristic of the eye, the unit comprising a second image-pickup optical system comprising a second image-pickup element which picks up an image of the anterior segment of the eye in order to observe the anterior segment of the eye, and a second alignment optical system for performing alignment between the anterior-segment image picked up by the second image-pickup element and a second center axis, which is positioned at a different height from the first center axis with respect to the eye, so as to have a predetermined relationship, an up-and-down movement mechanism which moves the body of the apparatus in the up-and-down direction with respect to the eye, a display device capable of displaying the anterior-segment image based on an image-pickup signal outputted from the first image-pickup element and the anterior-segment image based on an image-pickup signal outputted from the second image-pickup element, mode switching means which generates a mode switching signal for switching between a first measurement mode in which the first eye characteristic of the eye is measured by the first measurement unit and a second measurement mode in which the second eye characteristic of the eye is measured by the second measurement unit, and a control unit which is connected with the up-and-down movement mechanism and the display device, and controls the up-and-down movement mechanism and the display device, wherein the control unit drives and controls the up-and-down movement mechanism based on the mode switching signal generated by the mode switching means to change a state in which the first center axis and the eye are placed at substantially a same height into a state in which the second center axis and the eye are placed at substantially a same height by moving the main body of the apparatus by a distance between the first center axis and the second center axis in the up-and-down direction, and controls to display the image outputted from the first image-pickup element and the image outputted from the second image-pickup element simultaneously on the display device for a predetermined period of time during a shift from the first measurement mode to the second measurement mode based on the mode switching signal generated by the mode switching means.

Additional objects and advantages of the invention are set forth in the description which follows, are obvious from the description, or may be learned by practicing the invention. The objects and advantages of the invention may be realized and attained by the apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

FIGS. 3A to 3C are views showing changes in a form of the apparatus in switching of measurement modes of the apparatus according to the preferred embodiment of the present invention;

FIGS. 4A to 4C are views showing display control of a display monitor in the switching of the measurement modes.

DETAILED DESCRIPTION OF THE PREFERRED EMBODIMENTS

Figure 1:
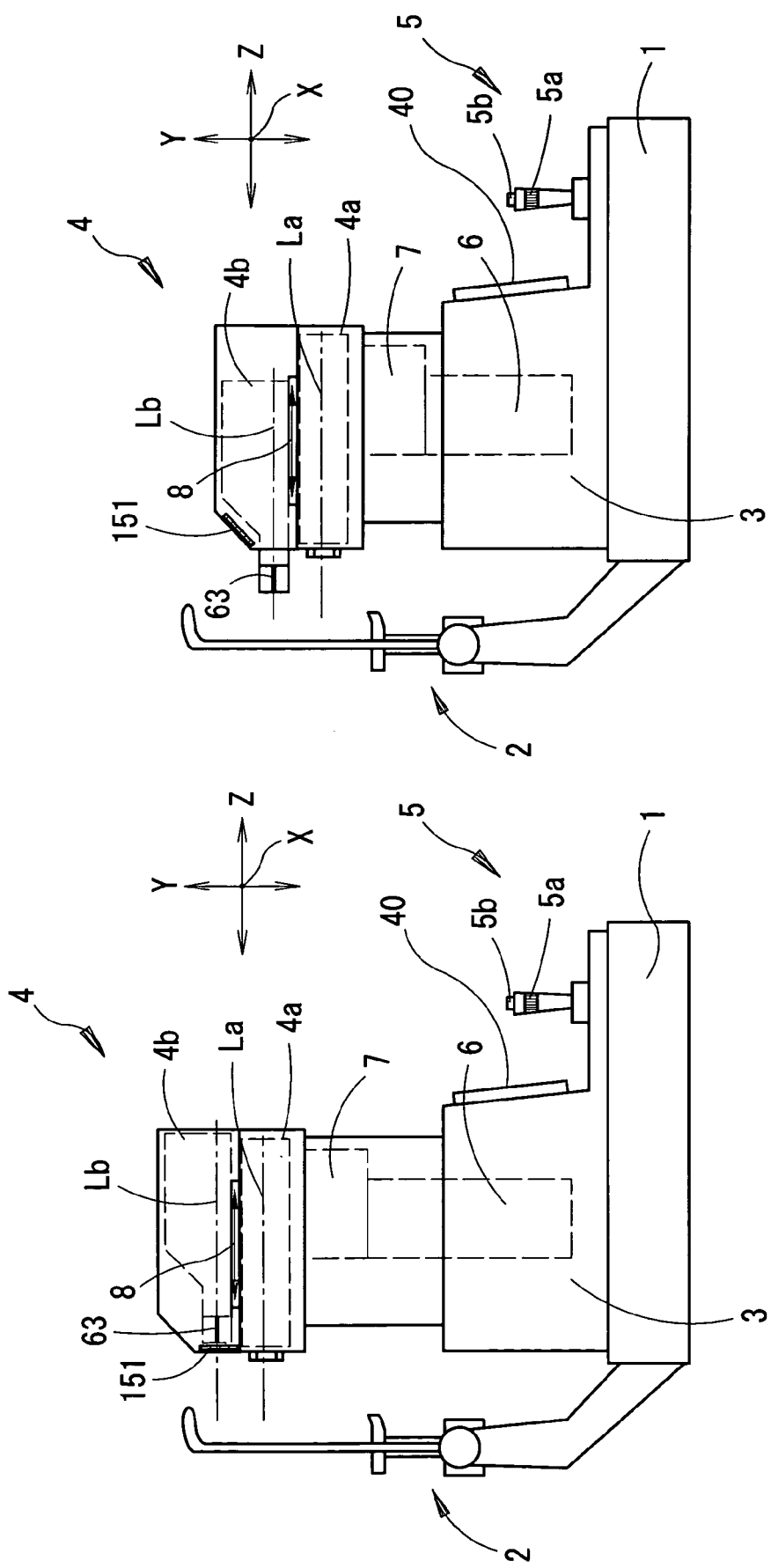
FIGS. 1A and 1B are external views showing an ophthalmic apparatus according to a preferred embodiment of the present invention.

A detailed description of one preferred embodiment of an ophthalmic apparatus embodied by the present invention is provided below with reference to the accompanying drawings. An ophthalmic apparatus which measures intraocular pressure, eye refractive power, and a corneal shape is herein used as an example. FIGS. 1A and 1B are external views showing an ophthalmic apparatus according to a preferred embodiment of the present invention. FIG. 1A shows a state of the apparatus when measuring the eye refractive power and the corneal shape, while FIG. 1B shows a state of the apparatus when measuring the intraocular pressure.

The ophthalmic apparatus comprises a base 1, a face supporting unit 2 attached to the base 1, a mobile base 3 provided on the base 1 and movable with respect to the base 1, and a measurement part 4 movable with respect to the mobile base 3. The measurement part 4 includes an eye refractive power/cornel shape measurement unit 4a (hereinafter referred to as a Ref-Kerato measurement unit) which performs measurement of the eye refractive power and the corneal shape (hereinafter referred to as a first eye characteristic) of an examinee's eye E, and an intraocular pressure measurement unit 4b which performs noncontact measurement of the intraocular pressure (hereinafter referred to as a second eye characteristic) of the eye E. The intraocular pressure measurement unit 4b is provided on the Ref-Kerato measurement unit 4a. Therefore, in the measurement part 4, a measurement optical axis La of the Ref-Kerato measurement unit 4a and a measurement optical axis Lb of the intraocular pressure measurement unit 4b differ in height. The measurement optical axis La or the measurement optical axis Lb is aligned with the eye E, thereby enabling measurement of the first eye characteristic or the second eye characteristic of the eye E.

By a Y driving unit 6 (an up-and-down movement unit) provided on the mobile base 3, the measurement part 4 is moved in an up-and-down direction (a Y-direction in FIGS. 1A and 1B) with respect to the eye E. The Y driving unit 6 moves the measurement part 4 in the Y-direction with respect to the eye E so that the measurement optical axis La or the measurement optical axis Lb is positioned at substantially the same height as the eye E.

In addition, by an XZ driving unit 7 provided on the Y driving unit 6, the measurement part 4 is moved in a right-and-left direction (an X-direction) and a back-and-forth (a working distance) direction (a Z-direction) with respect to the eye E. Accordingly, the measurement part 4 is movable in a three-dimensional direction of the X-, Y- and Z-directions. The Y driving unit 6 and the XZ driving unit 7 may be configured such that an X table movable in the X-direction is provided on a Y table movable in the Y-direction, a Z table movable in the Z-direction is provided on the X table, and the tables are moved by drive and control of respective motors for X, Y and Z tables.

The intraocular pressure measurement unit 4b is placed movable in the Z-direction with respect to the Ref-Kerato measurement unit 4a by drive of a driving unit 8. The driving unit 8 moves the intraocular pressure measurement unit 4b toward the eye E in an intraocular pressure measurement mode. On the other hand, in a Ref-Kerato measurement mode, the driving unit 8 moves the intraocular pressure measurement unit 4b away from the eye E. The driving unit 8 moves at least a nozzle 63 in the Z-direction. That is, a position of the end of the nozzle 63 is changed between a use position and a storage position by the driving unit 8.

By operating a joystick 5, the mobile base 3 is moved in the X- and Z-directions on the base 1. When a rotation knob 5b is rotated by an examiner, the Y driving unit 6 is driven, and thus the measurement part 4 is moved in the Y-direction. On the tip of the joystick 5, a measurement starting switch 5b is provided. In addition, a display monitor 40 is provided on the mobile base 3.

A shutter panel 151 is used to cover (block) an opening (not shown) provided on the front side of the intraocular pressure measurement unit 4b. The shutter panel 151 can be opened and closed (be inserted and removed) in conjunction with the back-and-forth movement of the intraocular pressure measurement unit 4b by the driving unit 8.

Referring FIG. 2, optical systems and control systems of the ophthalmic apparatus and a fluid injection mechanism of the intraocular pressure measurement unit 4b are described below.

First, optical systems of the Ref-Kerato measurement unit 4a are described. An eye refractive power measurement optical system 10 is an optical system for measuring the eye refractive power of the eye E. The measurement optical system 10 includes a projection optical system for projecting a measurement target in a spot shape onto a fundus Ef of the eye E via a central pupillary portion of the eye E, and a photo-receiving optical system for picking up fundus reflection light in a ring shape reflected from the fundus Ef via a peripheral pupillary portion of the eye E and picking up a fundus reflection image in the ring shape by a two-dimensional image-pickup element. An output signal from the two-dimensional image-pickup element is inputted into a control unit 20.

A dichroic mirror 29 transmits a measurement light bundle to be used by the measurement optical system 10. The dichroic mirror 29 also leads a fixation target light bundle from a fixation target presenting optical system 30 to the eye E and leads reflection light reflected from an anterior segment of the eye E to an observation optical system 50.

The fixation target presenting optical system 30 includes a visible light source 31 for fixation target presentation, a fixation target plate 32 having a fixation target, a projection lens 33, a total reflection mirror 34, a dichroic mirror 35, and an objective lens 36 for observation. Light from the fixation target presenting optical system 30 is made coaxial with the optical axis La. The dichroic mirror 35 has properties of transmitting visible light and reflecting infrared light. The visible light source 31 is in a position optically conjugate with the fundus Ef. By moving the visible light source 31 and the fixation target plate 32 in the direction of the optical axis, the eye E is fogged.

In front of the anterior segment of the eye E, a ring target projection optical systems 45 for emitting near infrared light for projecting a ring target onto a cornea Ec of the eye E, and a working-distance target projection optical systems 46 for emitting near infrared light for projecting infinite-distance targets onto the cornea Ec and thereby detecting an alignment state in the working-distance direction with respect to the eye E, are placed symmetrically with respect to the optical axis La. In addition to being used as an optical system for projecting the ring target for measuring the corneal shape of the eye E, the ring target projection optical systems 45 is also used as an optical system for projecting a target for the alignment state detection and an optical system for illuminating the anterior segment of the eye E.

The observation optical system 50 for picking up an image of the anterior segment of the eye E, shares the objective lens 36 and the dichroic mirror 35 with the fixation target presenting optical system 30. The observation optical system 50 further includes an image-pickup lens 51 and a two-dimensional image-pickup element 52 which are placed on an optical axis in a reflecting direction of the dichroic mirror 35. An output signal from the image-pickup element 52 is inputted into the control unit 20. Consequently, the image of the anterior segment of the eye E, which is illuminated by the ring target projection optical system 45, is picked up by the image-pickup element 52 via the dichroic mirror 29, the objective lens 36, the dichroic mirror 35, and the image-pickup lens 51, and then displayed on the monitor 40. The observation optical system 50 also serves as an image-pickup optical system for picking up an image of the ring target R formed on the cornea Ec of the eye E and images of the alignment targets M formed by the projection optical systems 46. Positions of the ring target image and the alignment target images are detected by the control unit 20.

Figure 2:
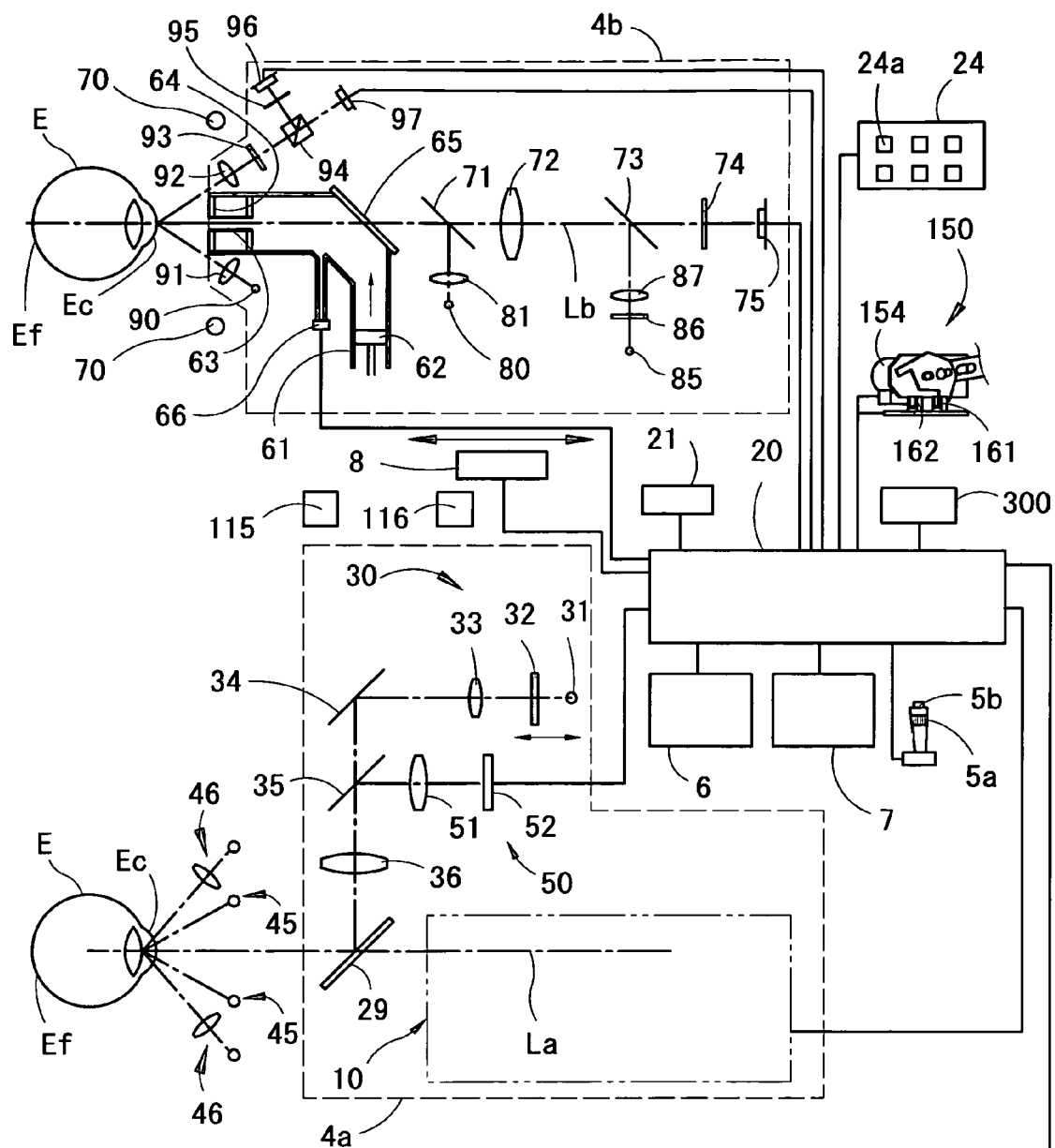
FIG. 2 is a view showing optical systems and control systems of a Ref-Kerato measurement unit and an intraocular pressure measurement unit.

The air (fluid) injection mechanism of the intraocular pressure measurement unit 4b is described referring to FIG. 2. A piston 62 is moved inside a cylinder 61 for air compression by driving force of a rotary solenoid (not shown). Air compressed in the cylinder 61 by the movement of the piston 62 is injected toward the cornea Ec of the eye E via the nozzle 63. The nozzle 63 is held by transparent glass plates 64. A glass plate 65 provided behind the nozzle 63 is also transparent. Behind the glass plate 65, an optical system for observation and alignment is placed (a detailed description will be given later). A pressure sensor 66 detects pressure in the cylinder 61. An output signal from the pressure sensor 66 is inputted into the control unit 20 and used to calculate an intraocular pressure value.

Next, optical systems of the intraocular pressure measurement unit 4b are described below. When using the intraocular pressure measurement unit 4b (in the intraocular pressure measurement mode), the nozzle 63 provided in the intraocular pressure measurement unit 4b protrudes toward the eye E relative to the front side of the Ref-Kerato measurement unit 4a.

Four infrared light sources 70 for illuminating the anterior segment of the eye E are placed having the optical axis Lb, which coincides with an axial line of the nozzle 63, at their center. An image of the anterior segment of the eye E formed by the light sources 70 is picked up by a two-dimensional image-pickup element 75 via the glass plate 65, a half mirror 71, an objective lens 72, a dichroic mirror 73 and a filter 74. In other words, the intraocular pressure measurement unit 4b comprises an optical system for picking up the image of the anterior segment of the eye E. The dichroic mirror 73 has properties of transmitting infrared light and reflecting visible light. The filter 74 has properties of transmitting light from the light source 70 and a light source 80 and not transmitting light from a light source 90. The anterior-segment image picked up by the two-dimensional image-pickup element 75 is displayed on the monitor 40 via the control unit 20.

The infrared light source 80 is used for alignment in the X- and Y-directions. The light emitted from the light source 80 is projected onto the cornea Ec from the front via a projection lens 81, the half mirror 71, and the glass plate 65. A corneal reflection image by the light source 80 is picked up by the image-pickup element 75 via the glass plate 65 to the filter 74. An output signal from the image-pickup element 75 is inputted into the control unit 20 and used for the alignment in the X- and Y-directions. Alternatively, corneal reflection images by the light sources 70 may be used for the alignment in the X- and Y-directions (for details, see U.S. Pat. No. 6,022,108 corresponding to Japanese Patent Application Unexamined Publication No. Hei10-71122, which is filed by the same applicant as the present invention). Light passing through a fixation target plate 86, which is illuminated by a visible light source 85 for fixation target projection, heads for the eye E via a projection lens 87, the dichroic mirror 73, the objective lens 72, the half mirror 71, and the glass plate 65.

The light emitted from the infrared light source 90 for detecting a deformation state of the cornea Ec is converted into substantially parallel light by a collimator lens 91 and then projected onto the cornea Ec. A corneal reflection image by the light source 90 is photo-received on a photodetector 96 via a photo-receiving lens 92, a filter 93, a half mirror 94, and a pinhole plate 95. The filter 93 has properties of transmitting the light from the light source 90 and not transmitting the light from the light source 70 and the light source 80. These optical systems are placed so that a photo-receiving amount of the photodetector 96 becomes maximum when the cornea Ec is in a predetermined deformation state (a flat state). An output signal from the photodetector 96 is inputted into the control unit 20 and used to calculate the intraocular pressure value.

The light source 90 and the collimator lens 91 are shared by a target projection system for detecting an alignment state in the Z-direction. The corneal reflection image by the light source 90 enters a one-dimensional position detector 97 such as a position sensitive detector (PSD) and a line sensor via the photo-receiving lens 92 to the half mirror 94. An output signal from the position detector 97 is inputted into the control unit 20 and used to detect the alignment state in the Z-direction. In other word, when the eye E (the cornea Ec) moves in the Z-direction, an incident position of the corneal reflection image by the light source 90 also moves on the position detector 97, and thereby the alignment state in the Z-direction with respect to the eye E is detected based on the detection signal from the position detector 97.

In FIG. 2, the optical system for detecting the deformation state of the cornea Ec and the optical system for detecting a working distance are illustrated as if they are arranged in the up-and-down direction for the sake of convenience; however, they are actually arranged in the right-and-left direction with respect to the eye E.

Next, a configuration of the control system is described below. The control unit 20, which performs operations such as control of the entire apparatus and calculation of measurement values, is connected with elements of the Ref-Kerato measurement unit 4a and the intraocular pressure measurement unit 4b, the monitor 40, the Y driving unit 6, the XZ driving unit 7, the driving unit 8, a memory 21 which stores data such as measurement results, the rotation knob 5a, the measurement starting switch 5b, a switch unit 24 with various switches such as a measurement mode selecting switch 24a, and others. A detection unit 300 detects that the mobile base 3 moves to a predetermined backward position. A micro switch, for example, is used as the detection unit 300, and the detection unit 300 is used for switching of the measurement modes (for details, see US-2004-0189936-A1 corresponding to Japanese Patent Application Unexamined Publication No. 2004-313758). A shutter inserting/removing mechanism 150 inserts and removes the shutter panel 151 into and from the front of the nozzle 63 placed in the storage position. To be specific, the shutter inserting/removing mechanism 150 comprises a driving unit (a motor 154) for opening and closing the shutter panel 151 and a converting mechanism for converting a driving force of the motor 154 into an open/close operation of the shutter panel 151. A first photosensor 161 detects that the shutter panel 151 is closed, while a second photosensor 162 detects that the shutter panel 151 is opened. For details of a configuration of the shutter inserting/removing mechanism, see Japanese Patent Application Unexamined Publication No. 2008-99968, which is filed by the same applicant as the present invention. A protrusion (projection) detecting unit 115 detects a protruding movement of the intraocular pressure measurement unit 4b, while a retreat detecting unit 116 detects a retreating movement of the intraocular pressure measurement unit 4b.

The image-pickup elements 52 and 75 are connected to the control unit 20. The image-pickup element 52 picks up the anterior-segment image in the Ref-Kerato measurement mode which uses the Ref-Kerato measurement unit 4a. In other words, the image-pickup element 52 functions as anterior-segment image-pickup means for the Ref-Kerato measurement unit 4a. The image picked up by the image-pickup element 52 is displayed on the monitor 40 for anterior-segment observation in the Ref-Kerato measurement mode. This image is mainly used to perform alignment of the measurement optical axis La with respect to the eye E. On the other hand, the image-pickup element 75 picks up the anterior-segment image in the intraocular pressure measurement mode which uses the intraocular pressure measurement unit 4b. In other words, the image-pickup element 75 functions as anterior-segment image-pickup means for the intraocular pressure measurement unit 4b. The image picked up by the image-pickup element 75 is displayed on the monitor 40 for anterior-segment observation in the intraocular pressure measurement mode. This image is mainly used to perform alignment of the measurement optical axis Lb with respect to the eye E.

Operations of the ophthalmic apparatus having the foregoing configuration are described below. In the preferred embodiment of the present invention, a case in which the intraocular pressure is measured after Ref-Kerato measurement is performed is described.

In this case, first the Ref-Kerato measurement is performed. The control unit 20 drives the Y driving unit 6 so that the measurement optical axis La and the eye E are positioned at substantially a same height (rough positioning is sufficient). Here, the control unit 20 controls to adjust a height position of the measurement part 4 so that an eye-level conformation line formed on the face supporting unit 2 and the measurement optical axis La are positioned at substantially the same height. In addition, the control unit 20 drives the driving unit 8 to retreat the intraocular pressure measurement unit 4b toward a main body of the apparatus relative to the Ref-Kerato measurement unit 4a (controls to move the intraocular pressure measurement unit 4b away from the eye E) so that the end of the nozzle 63 is kept from contact with a part of the examinee such as a forehead during the Ref-Kerato measurement (see FIG. 3A). Further, the control unit 20 drives the XZ driving unit 7 to move the measurement part 4 to an original position with respect to the mobile base 3, and drives motor 154 to close the shutter panel 151. Accordingly, when the nozzle 63 is placed inside the body of the apparatus, the opening formed on the front side of the measurement part 4 is blocked by the shutter panel 151. As above, a state in which the Ref-Kerato measurement can be performed is attained (see FIG. 1A).

In the Ref-Kerato measurement, a case in which first a right eye is measured and then a left eye is measured is described below. First, alignment of the Ref-Kerato measurement unit 4a in the X-, Y-, and Z-directions with respect to a right eye ER of the eye E is performed. The examiner performs rough alignment by operating the joystick 5 and the rotation knob 5a while observing the monitor 40. Consequently, an image F1 (the anterior-segment image) of the eye E picked up by the image-pickup element 52 is displayed on the monitor 40, and then the ring target image R by the ring target projection optical system 45 and the infinite-distance target images M by the working-distance projection optical system 46 are brought to a state of being picked up by the image-pickup element 52 (see FIG. 2). A reticle LT is used as an alignment reference for manual alignment.

The control unit 20 detects an alignment state in the X- and Y-directions and an alignment state in the Z-direction of the Ref-Kerato measurement unit 4a with respect to the eye E. Then, the control unit 20 drives and controls the Y driving unit 6 and the XZ driving unit 7 to automatically move the measurement part 4 in the X-, Y-, and Z-directions based on detection results of the alignment states (automatic alignment). This enables fine alignment between the eye E and the Ref-Kerato measurement unit 4a. The control unit 20 can obtain an amount of alignment deviation of the Ref-Kerato measurement unit 4a in the X- and Y-directions with respect to the eye E by calculating coordinates of the center position of the ring target image R detected by the image-pickup element 52. In addition, by using characteristics that when the measurement part 4 deviates in the Z-direction (the working-distance direction) with respect to the eye E, a space of the ring target image R in a predetermined meridional direction changes while a distance between the infinite-distance target images M hardly changes, the control unit 20 can obtain an amount of alignment deviation of the Ref-Kerato measurement unit 4a in the Z-direction with respect to the eye E.

When the alignment in the X-, Y-, and Z-directions with respect to the eye E is completed as above, the measurement automatically starts. If an automatic shot is OFF, the measurement starts when the alignment is completed and the measurement starting switch 5b is pressed by the examiner.

The control unit 20 first measures the corneal shape of the eye E based on a shape of the ring target image R picked up by the image-pickup element 52 and controls to display measurement results of the corneal shape on the monitor 40. Then, when a predetermined number of (e.g., three) measurement values of the corneal shape except measurement errors are obtained, a shift to eye refractive power measurement is performed.

The control unit 20 controls to light the measurement light source provided in the measurement optical system 10 based on input of the measurement starting signal. The measurement light emitted from the measurement light source is projected onto the fundus Ef of the eye E via a projection optical system (not shown) of the measurement optical system 10 and the dichroic mirror 29, and forms a point light source image in a spot shape on the fundus Ef.

The light of the point light source image formed on the fundus Ef is reflected and scattered to exit the eye E, passes through the dichroic mirror 29, and is photo-received on the image-pickup element as a ring image via the photo-receiving optical system (not shown) of the measurement optical system 10.

At this time, preliminary measurement of the eye refractive power is first performed. Then, based on results of the preliminary measurement, the light source 31 and the fixation target panel 32 are moved in the optical axis direction, and thereby the eye E is fogged. Then, the eye refractive power measurement is performed on the fogged eye E.

The output signal from the image-pickup element of the measurement optical system 10 is stored as image data in the memory 21. The control unit 20 then calculates values of the eye refractive power, sphere power (S), cylinder power (C), and an astigmatic axial angle (A). The measurement results are displayed on the monitor 40. When a predetermined number of (e.g., three) measurement values except measurement errors are obtained, the eye refractive power measurement terminates.

When a predetermined condition for measurement termination is satisfied (e.g., a predetermined number of measurement values are obtained in both the eye refractive power measurement and the corneal shape measurement), the measurement of the right eye ER becomes completed.

When the measurement of the right eye ER is completed, characters "FINISH" indicating the measurement completion are displayed on the monitor 40. With this indication, the examiner shifts to measurement of the left eye EL. At this time, the control unit 20 drives the XZ driving unit 7 to return the measurement part 4 to the original position with respect to the mobile base 3.

The examiner operates the joystick 5 to move the mobile base 3 in the right direction with respect to the base 1, thereby moving the measurement part 4 in the direction of the left eye EL of the eye E. Then, similarly to the measurement of the right eye ER, alignment between the left eye EL and the Ref-Kerato measurement unit 4a is performed by rough alignment of the Ref-Kerato measurement unit 4a with the left eye EL through manual operation by the examiner and automatic alignment of the Ref-Kerato measurement unit 4a with the left eye EL by the drive and control by the control unit 20.

When the alignment is completed as above, the measurement of the left eye EL is automatically performed. The control unit 20 measures the corneal shape and the eye refractive power of the left eye EL in the same manner as the measurement of the right eye ER. When the predetermined condition for measurement termination is satisfied, the measurement of the left eye EL becomes completed.

FIG. 3A shows a positional relationship between the measurement part 4 and the eye E during and after the Ref-Kerato measurement. When a measurement completion signal is generated, the control unit 20 controls to display a message on the monitor 40 indicating that the mobile base 3 is to be moved backward when seen from the examinee. By this indication, the examiner operates the joystick 5 to move the mobile base 3 backward. Accordingly, switching from the Ref-Kerato measurement mode to the intraocular pressure measurement mode becomes permitted with a detection signal from the detection unit 300 which detects that the mobile base 3 is moved to the predetermined backward position, and the control unit 20 controls to generate a measurement mode switching signal. Alternatively, the control unit 20 may control to perform the switching to (selection of) the intraocular pressure measurement mode when both the detection signal from the detection unit 300 and an operation signal from the measurement mode selecting switch 24a are inputted (manual switching).

Figure 5:
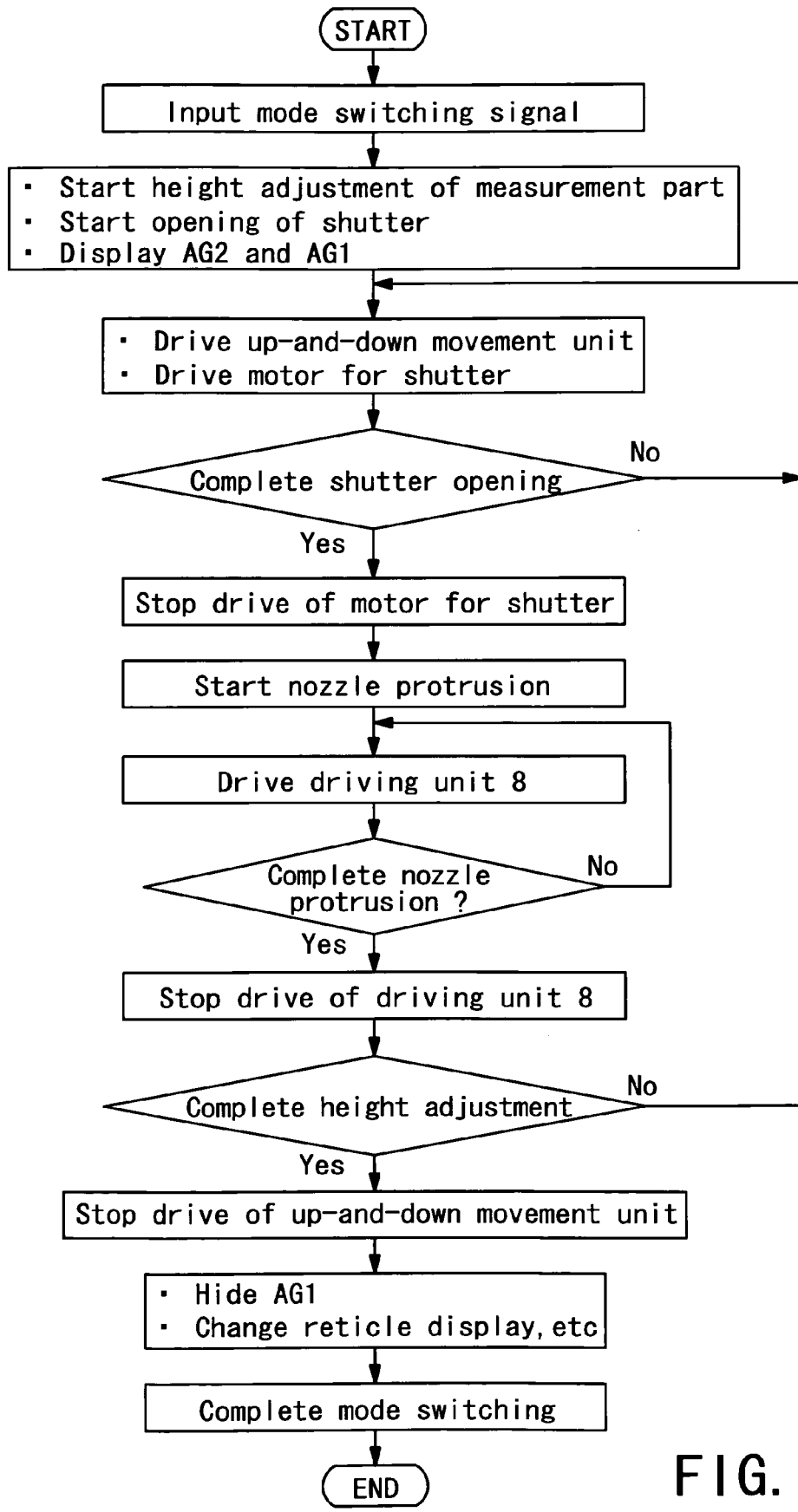
FIG. 5 is a flowchart illustrating operations of the apparatus after a measurement mode switching signal is generated.

FIG. 5 is a flowchart illustrating operations of the apparatus after the measurement mode switching signal is generated. The control unit 20 drives and controls the Y driving unit 6 and controls a display of the monitor 40 based on the measurement mode switching signal. More specifically, when the switching signal to the intraocular pressure measurement mode is inputted (generated), the control unit 20 drives the Y driving unit 6 to move the measurement part 4 downward so that the measurement optical axis Lb of the intraocular pressure measurement unit 4b and the eye E are positioned at substantially a same height (rough positioning is sufficient).

In the above operation, the control unit 20 controls to move the measurement part 4 downward (drives the Y driving unit 6) by a distance between the measurement optical axis La and the measurement optical axis Lb with respect to the height position of the measurement part 4 after the Ref-Kerato measurement. For that purpose, it is sufficient that the distance between the measurement optical axis La and the measurement optical axis Lb is pre-stored in the memory 21.

When the switching signal to the intraocular pressure measurement mode is inputted, the control unit 20, while driving and controlling the Y driving unit 6 based on the measurement mode switching signal, controls to set an image obtained by the measurement unit used in the measurement mode after switching (the intraocular pressure measurement unit 4b) as a main image (a display window AG2 in FIGS. 4A, 4B and 4C). Simultaneously, the control unit 20 controls to display an image obtained by the other measurement unit (the Ref-Kerato measurement unit 4a) on the monitor 40 as a sub-image (a display window AG1 in the FIGS. 4A and 4B), which is made smaller than the main image (see FIG. 4A). More specifically, the control unit 20 controls to switch the image displayed as the main image on the monitor 40 from the image picked up by the image-pickup element 52 to the image picked up by the image-pickup element 75, and simultaneously controls to display the image which has been displayed as the main image on the upper right end of the image picked up by the image-pickup element 75.

When the switching signal to the intraocular pressure measurement mode is inputted, the control unit 20 also drives the motor 154 so that the shutter panel 151 is removed from the front of the nozzle 63. In this operation, when a detection signal from the second photosensor 162 is inputted, the control unit 20 determines that the shutter panel 151 is opened and stops driving the motor 154. Accordingly, the intraocular pressure measurement unit 4b becomes movable toward the eye E. Then, the control unit 20 drives the driving unit 8 to move the intraocular pressure measurement unit 4b toward the eye E so that the end of the nozzle 63 is positioned on the eye E's side (protruded) relative to the front side of the Ref-Kerato measurement unit 4a. Upon receiving a detection signal from the protrusion (projection) detecting unit 115, the control unit 20 determines that the nozzle 63 is protruded to the use position and stops driving the driving unit 8. The shutter panel 151 is still closed immediately after the input of the measurement mode changing signal. Therefore, the back of the shutter panel 151 is displayed on the display window AG2 (the anterior-segment image is not displayed); however, the anterior-segment image comes to be displayed as the shutter panel 151 opens. Meanwhile, the image F1 is displayed on the display window AG1, enabling the examiner to observe the eye E.

When the Y driving unit 6 is driven by the drive and control by the control unit 20 and the measurement part 4 is moved downward, the height of the Ref-Kerato measurement unit 4a deviates from the height of the eye E. Accordingly, the image F1 displayed on the display window AG1 thus is moved toward the top of the screen. When the measurement part 4 is further moved downward, the eye E falls outside an image-pickup range of the image-pickup element 52. Consequently, a part of the examinee such as a cheek comes to be displayed on the display window AG1.

Meanwhile, the intraocular pressure measurement unit 4b is moved toward the eye E by the downward movement of the measurement part 4. When the eye E comes to fall within an image-pickup range of the image-pickup element 75, an image (the anterior-segment image) F2 of the eye E picked up by the image-pickup element 75 is displayed on the display window AG2. A timing in which the image F2 becomes displayable varies depending on time needed for the open movement of the shutter panel 151. However, in the preferred embodiment of the present invention, the time between when the measurement mode switching signal is inputted and when the shutter panel 151 is opened is set shorter than the time between when the measurement mode switching signal is inputted and when an upper part of the eye E comes to fall within the image-pickup range of the image-pickup element 75. Accordingly, the image F2 can be displayed on the monitor 40 at the same instant when the eye E comes to fall within the image-pickup range of the image-pickup element 75.

FIG. 3B shows a positional relationship between the apparatus and the eye E when the anterior-segment image of the eye E is picked up by the image-pickup element 75 when the measurement mode switching is in progress. FIG. 4B shows a display screen of the monitor 40 which corresponds to the positional relationship in the FIG. 3B. In this case, the upper half of the eye is displayed on the display window AG2, and the cheek of the examinee is displayed on the display window AG1. In the preferred embodiment of the present invention, while the display screen is as shown in the FIG. 4B, the display condition may vary depending on factors such as the distance between the measurement optical axis La and the measurement optical axis Lb in the up-and-down direction, and the image-pickup ranges of the image-pickup element 52 and the image-pickup element 75.

As the measurement part 4 is further moved downward, the measurement optical axis Lb and the eye E come to be placed at substantially the same height (see FIG. 3C). When the measurement part 4 is moved by the distance between the optical axes La and Lb, which is pre-stored in the memory 21, from the height position after the Ref-Kerato measurement, the control unit 20 stops driving of the Y driving unit 6. The height adjustment of the measurement part 4 is completed as above. FIG. 3C shows a positional relationship between the apparatus and the eye E after completing the height adjustment of the measurement part 4. FIG. 4C shows a display screen of the monitor 40 after completing the height adjustment of the measurement part 4.

The control unit 20 controls to hide the display window AG1 after completing the height adjustment of the measurement part 4 which is performed for shifting to the intraocular pressure measurement, and continually controls to display the display window AG2 on the monitor 40. In other words, the control unit 20 controls to remove the sub-image from the monitor 40 when the drive and control of the Y driving unit 6 based on the measurement mode switching is stopped. At this time, the control unit 20 controls to changes indications such as the reticle LT and measurement results to those for the intraocular pressure measurement. In the above control operation, it is sufficient that the image picked up by the Ref-Kerato measurement unit 4a and the image picked up by the intraocular pressure measurement unit 4b are simultaneously displayed on display means for a predetermined period of time after starting the drive and control for the shifting to the intraocular pressure measurement. For example, the display window AG1 may be hidden on the monitor 40 when the eye E comes to fall outside the image-pickup range of the image-pickup element 52.

In the preferred embodiment of the present invention, the apparatus is set so that the time between when the measurement mode switching signal is inputted and when the forward movement of the nozzle 63 is completed is shorter than the time between when the measurement mode switching signal is inputted and when the height adjustment of the measurement part 4 is completed. Accordingly, by the time the height adjustment of the measurement part 4 is completed, the forward movement of the nozzle 63 is completed, and the working distance between the intraocular pressure measurement unit 4b and the eye E becomes substantially appropriate. Consequently, the unblurred, clear eye image is displayed on the display window AG1 on the monitor 40. With the operation described above, the apparatus is brought into a form in which the intraocular pressure can be measured (see FIG. 3C). Alternatively, the control unit 20 may control to perform the forward movement of the nozzle 63 after the height adjustment of the measurement part 4.

As shown above, during the drive and control of the Y driving unit 6 based on the measurement mode switching (switching of the apparatus forms in accordance with the measurement mode switching), the image picked up by the Ref-Kerato measurement unit (a first measurement unit) 4a and the image picked up by the intraocular pressure measurement unit (a second measurement unit) 4b, which is placed at a different height from the Ref-Kerato measurement unit 4a, are simultaneously displayed on the monitor 40. A wide observation range on the anterior segment of the eye E is thus obtained. This facilitates for the examiner to confirm conditions such as a condition of the eye E (e.g. a condition of eye fixation) and a supporting condition of the examiner's face by the face supporting unit 2. Accordingly, the examiner can promptly react to a sudden movement of the examinee or other events. In the foregoing display control of the images, both the display window AG1 and the display window AG2 may be displayed on a two-part split screen. Alternatively, the display window AG1 may be displayed larger than the display window AG2. Still alternatively, the above display control conditions may be selected arbitrarily.

In the foregoing mode switching, when the image displayed as the main image is switched from the image picked up by the image-pickup element 52 to the image picked up by the image-pickup element 75 during or after the height adjustment of the measurement part 4, the image may possibly be moved upward or downward causing the examiner to be confused. To be specific, this may give an impression as if the measurement optical axis La of the Ref-Kerato measurement unit 4a returns to the height of the eye E.

Hence, in the preferred embodiment of the present invention, the control unit 20 controls to display the image picked up by the image-pickup element 75 as the main image at the time when the measurement mode switching signal is inputted after completing the Ref-Kerato measurement. This enables the examiner to smoothly perform the alignment operation and the intraocular pressure measurement after the height adjustment of the measurement part 4 is performed and the intraocular pressure measurement becomes performable. In addition, if the image picked up by image-pickup element 75 is displayed on the monitor 40 at the time when the measurement mode switching signal is inputted as described above, the back of the shutter panel 151 is initially displayed (if the shutter panel 151 is not provided, the forehead of the examinee is displayed), and thus the anterior-segment image cannot be displayed on the monitor 40. However, by displaying the image picked up by the image-pickup element 52 as the sub-image as above, the anterior-segment image becomes observable on the monitor 40.

In order to reduce a load on the control unit 20, instead of displaying the moving image picked up in real time, it is also possible that images captured serially are displayed one after another (updated) as the sub-image on the monitor 40.

Operations after the shift to the intraocular pressure measurement mode (after the shift to the apparatus form in which the intraocular pressure can be measured) are described below.

Alignment of the intraocular pressure measurement unit 4b in the X-, Y-, and Z-directions with respect to the left eye EL of the eye E is performed. The examiner operates the joystick 5 while observing the monitor 40 to perform rough alignment of the intraocular pressure measurement unit 4b in the X- and Z-directions with respect to the left eye EL. When achieving a state where the corneal reflection image by the light source 90 enters the position detector 97, the control unit 20 drives and controls the XZ driving unit 7 based on a detection result to perform fine alignment in the Z-direction. In addition, the control unit 20 drives and controls the XZ driving unit 7 and the Y driving unit 6 based on a detection result of the corneal reflection image by the light source 80 of the image-pickup element 75 to perform fine alignment in the X- and Y-directions.

When the alignment states of the intraocular pressure measurement unit 4b in the X-, Y-, and Z-directions with respect to the left eye EL fall within respective allowable ranges, the control unit 20 controls to automatically generate a trigger signal (or display on the monitor 40 an indication that the alignment is completed so that the examiner presses the measurement starting switch 5b to input the trigger signal) and drives the rotary solenoid (not shown). When the piston 62 is moved by the drive of the rotary solenoid, the air inside the cylinder 61 is compressed, and the compressed air is blown from the nozzle 63 toward the cornea Ec. The cornea Ec is gradually deformed by the blowing of the compressed air, and when brought to the flat state, the maximum amount of the light enters the photodetector 96. The control unit 20 obtains the intraocular pressure value based on the output signal from the pressure sensor 66 and the output signal from the photodetector 96. This measurement result is displayed on the monitor 40. When the predetermined condition for measurement termination is satisfied, the measurement of the left eye EL becomes completed. After the completion of the measurement of the left eye EL, the examiner shifts to measurement of the right eye ER.

The examiner pulls the joystick 5 once and moves the nozzle 63 to the front of the right eye ER. The control unit 20 drives the XZ driving 7 to return the measurement part 4 to the original position (in X- and Z-directions) with respect to the mobile base 3.

Then, the examiner performs alignment of the intraocular pressure measurement unit 4b in the X-, Y-, and Z-directions with respect to the right eye ER. The examiner operates the joystick 5 while observing the monitor 40 to perform rough alignment. In this case, alignment between the right eye ER and the intraocular pressure measurement unit 4b is performed, similarly to the intraocular pressure measurement of the left eye EL, by the rough alignment between the intraocular pressure measurement unit 4b and the right eye ER through the manual operation by the examiner, and automatic alignment of the intraocular pressure measurement unit 4b with the eye E by the drive and control by the control unit 20. When the alignment is completed as above, the intraocular pressure measurement of the right eye ER is automatically performed.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus comprising:
   a first measurement unit placed in a main body of the apparatus, which measures a first eye characteristic of an examinee's eye, the unit comprising
      a first image-pickup optical system comprising a first image-pickup element which picks up an image of an anterior segment of the eye in order to observe the anterior segment of the eye, and
      a first alignment optical system for performing alignment between the anterior-segment image picked up by the first image-pickup element and a first center axis so as to have a predetermined relationship;
   a second measurement unit placed in the main body of the apparatus in a position in an up-and-down direction with respect to the first measurement unit, which measures a second eye characteristic of the eye, the unit comprising
      a second image-pickup optical system comprising a second image-pickup element which picks up an image of the anterior segment of the eye in order to observe the anterior segment of the eye, and
      a second alignment optical system for performing alignment between the anterior-segment image picked up by the second image-pickup element and a second center axis, which is positioned at a different height from the first center axis with respect to the eye, so as to have a predetermined relationship;
   an up-and-down movement mechanism which moves the body of the apparatus in the up-and-down direction with respect to the eye;
   a display device capable of displaying the anterior-segment image based on an image-pickup signal outputted from the first image-pickup element and the anterior-segment image based on an image-pickup signal outputted from the second image-pickup element;
   mode switching means which generates a mode switching signal for switching between a first measurement mode in which the first eye characteristic of the eye is measured by the first measurement unit and a second measurement mode in which the second eye characteristic of the eye is measured by the second measurement unit; and
   a control unit which is connected with the up-and-down movement mechanism and the display device, and controls the up-and-down movement mechanism and the display device, wherein
   the control unit drives and controls the up-and-down movement mechanism based on the mode switching signal generated by the mode switching means to change a state in which the first center axis and the eye are placed at substantially a same height into a state in which the second center axis and the eye are placed at substantially a same height by moving the main body of the apparatus by a distance between the first center axis and the second center axis in the up-and-down direction, and controls to display the image outputted from the first image-pickup element and the image outputted from the second image-pickup element simultaneously on the display device for a predetermined period of time during a shift from the first measurement mode to the second measurement mode based on the mode switching signal generated by the mode switching means.

2. The ophthalmic apparatus according to claim 1, wherein the control unit controls to display the image outputted from the first image-pickup element and the image outputted from the second image-pickup element simultaneously on the display device for a period of time from when the mode switching signal is generated by the mode switching means to when the eye falls outside an image-pickup range of the first image-pickup element.

3. The ophthalmic apparatus according to claim 1, wherein the control unit controls to display the image outputted from the first image-pickup element and the image outputted from the second image-pickup element simultaneously on the display device for a period of time from when the mode switching signal is generated by the mode switching means to when the first measurement mode is shifted to the second measurement mode.

4. The ophthalmic apparatus according to claim 1, wherein the control unit controls to display the image outputted from the second image-pickup element as a main image and display the image outputted from the first image-pickup element as a sub-image which is made smaller than the main image when displaying the image outputted from the first image-pickup element and the image outputted from the second image-pickup element simultaneously on the display device.

5. The ophthalmic apparatus according to claim 4, wherein the control unit controls to display the image outputted from the second image-pickup element as the main image when the mode switching signal is generated by the mode switching means.

6. The ophthalmic apparatus according to claim 1, further comprising:
- a back-and-forth movement mechanism which moves at least a part of the second measurement unit in a back-and-forth direction with respect to the first measurement unit, and
- a driving unit which opens and closes a shutter for covering an opening formed on the front side of the second measurement unit, wherein
- the control unit controls to open the shutter by driving and controlling the driving unit and move at least a part of the second measurement unit forward by driving and controlling the back-and-forth movement mechanism based on the mode switching signal generated by the mode switching means.

* * * * *